(12) United States Patent
Papadopoulos et al.

(10) Patent No.: US 9,116,159 B2
(45) Date of Patent: Aug. 25, 2015

(54) VEGF-A$_{121}$ ASSAY

(71) Applicant: Regeneron Pharmaceuticals, Inc., Tarrytown, NY (US)

(72) Inventors: Nicholas Papadopoulos, LaGrangeville, NY (US); Anthony Dore, Middletown, NY (US); Douglas MacDonald, New York, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 93 days.

(21) Appl. No.: 13/900,129

(22) Filed: May 22, 2013

(65) Prior Publication Data

US 2013/0315907 A1    Nov. 28, 2013

Related U.S. Application Data

(60) Provisional application No. 61/649,959, filed on May 22, 2012.

(51) Int. Cl.
*G01N 33/74* (2006.01)
*G01N 33/50* (2006.01)

(52) U.S. Cl.
CPC .......... *G01N 33/74* (2013.01); *G01N 2333/515* (2013.01); *G01N 2800/52* (2013.01)

(58) Field of Classification Search
CPC .............................. G01N 33/74; G01N 33/50
See application file for complete search history.

(56) References Cited

U.S. PATENT DOCUMENTS

| | | |
|---|---|---|
| 2005/0119165 A1 | 6/2005 | Jue et al. |
| 2013/0108626 A1 | 5/2013 | Delmar et al. |
| 2013/0115640 A1 | 5/2013 | Tumlin et al. |

FOREIGN PATENT DOCUMENTS

| | | |
|---|---|---|
| WO | 2011089101 A1 | 7/2011 |
| WO | 2012010546 A1 | 1/2012 |
| WO | 2012010547 A1 | 1/2012 |
| WO | 2012010548 A1 | 1/2012 |
| WO | 2012010549 A1 | 1/2012 |
| WO | 2012010550 A1 | 1/2012 |
| WO | 2012010551 A1 | 1/2012 |
| WO | 2012010552 A1 | 1/2012 |

OTHER PUBLICATIONS

Hegde P, Xing B, O'Day S et al. Biomarkers of treatment benefit in a randomized phase II study of bevacizumab in combination with carboplatin and paclitaxel in metastatic melanoma patients (BEAM). Journal of Clinical Oncology 2010; 28:15s Abstract No. 10563.
Jayson GC, de Haas S, Delmar P, et al. Evaluation of plasma VEGFA as a potential predictive pan-tumour biomarker for bevacizumab. 2011 European Multidisciplinary Cancer Congress. Abstract No. 804. Presented Sep. 24, 2011.
Abajo, A, et al, World J Gastroenterol, Feb. 21, 2012; 18(7): 637-645.
Bates, Do, et al. Clin Cancer Res 2012; 18:6384-6391. Published OnlineFirst Oct. 25, 2012.
Broll, R, et al. EJSO 2001; 27: 37-42.
Finley, SD and Popel, AS, Sep. 2013, The AAPS Journal. 14(3):500-509 (Epub May 1, 2012).
Hamerlik, P, et al., J. Exp. Med. 2012 209(3):507-520.
Lambrechts, D, et al., Mar. 20, 2013, J Clin Oncology, 31(9):1219-1230.
Mamluk, R, et al., 2002, J. Biol. Chem., 277(27):24818-24825 (Epub May 1, 2002).
Miles, DW, et al., Jul. 10, 2010, J Clin Oncology 28(20):3239-3247.
Nakamura, F, et al., 1998, Neuron, 21(5):1093-1100.
Paule, B, et al. 2010, PLoS ONE, 5(5): e10715.
Van Cutsem, E, et al, Jun. 10, 2012, J Clin Oncology, 30(17):2119-2127.
Zhang, Y, et al, 2012, Asian Pacific Journal of Tropical Medicine, 239-242.

*Primary Examiner* — Ruixiang Li
(74) *Attorney, Agent, or Firm* — Mary C. Johnson; Joseph Zahner

(57) ABSTRACT

The invention provides a method for determining the level of VEGF-A$_{121}$ isoform in a sample by selectively removing the VEGF-A$_{165}$ isoform from the sample using a neuropilin-1 pull-down procedure, then determining the total amount of VEGF-A remaining afterward. The invention provides methods of treating a patient suffering from a disease which may benefit from the administration of a VEGF antagonist by determining the level of VEGF-A$_{121}$ in the patient's circulation. Methods of diagnosis, prognosis, monitoring, and patient stratification are also provided.

15 Claims, No Drawings

VEGF-A$_{121}$ ASSAY

STATEMENT OF RELATED APPLICATIONS

This application claims the benefit under 35 U.S.C. §119 (e) of U.S. Provisional Application No. 61/649,959, filed 22 May 2012, which application is herein incorporated by reference.

FIELD OF THE INVENTION

The invention relates to assays for measuring a VEGF-A$_{121}$ isoform. The invention also relates to methods for treating patients with VEGF related diseases by predicting whether a patient is likely to respond to VEGF antagonist therapy by assessing the level of VEGF-A$_{121}$ in the patient's blood.

BACKGROUND OF THE INVENTION

Cancer is a collection of myriad diseases, each of which has a unique molecular signature and drug response profile. For example, colorectal cancer may be any one of hereditary nonpolyposis colorectal cancer, familial adenomatous polyposis, and Gardner syndrome. Furthermore, any particular cancer may be associated with distinct molecular lesions, such as wnt signaling dysregulation, p53 and other DNA repair and apoptosis dysregulation, growth factor signaling and other oncogene dysregulation, or any combination thereof. Thus, cancer, such as prostate cancer, breast cancer, colorectal cancer, lung cancer, or pancreatic cancer, may be further subdivided into specific molecular diseases, each of which has its own diagnostic or prognostic indicators and therapeutic responses.

There is a continuing medical need for specific tests to diagnose the particular nature of a cancer, and to determine whether a patient is likely to respond to a particular therapy. VEGF antagonists are a class of therapeutics intended to treat cancer by abrogating or otherwise altering the vascularization of tumors. The effectiveness of these drugs depends in part on the specific type of cancer and other factors associated with the physiology of the patient. The development of a prognostic biomarker assay or patient stratification protocol will enable the physician to select those patients who are most likely to respond favorably to therapy, and to monitor a patient's response to a therapy.

Several biomarkers can predict how a patient will respond to VEGF antagonist (e.g., aflibercept and bevacizumab) therapy. Those biomarkers include E-selectin, bFGF, ICAM, and VEGF (Calleri et al., Clin Cancer Res 2009, 15(24):7652-7657; Dowlati et al., Clin Cancer Res 2008, 14(5):1407-1412.) VEGF is found in several isoforms: VEGF-A$_{206}$, VEGF-A$_{189}$, VEGF-A$_{165}$, VEGF-A$_{145}$, VEGF-A$_{121}$, VEGF-B, VEGF-C and VEGF-D. VEGF-A$_{206}$, VEGF-A$_{189}$ and VEGF-A$_{165}$, bind to neuropilin-1 ("NRP1") as well as VEGF receptors 1 and 2 (reviewed in Neufeld et al., FASEB J., 1999, 13:9-22).

SUMMARY OF THE INVENTION

VEGF-A$_{165}$ and VEGF-A$_{121}$ are the predominant forms found in the circulation. VEGF-A$_{165}$ is subject to high patient-to-patient variability and is rapidly cleared from the circulation; and therefore its levels are not an accurate prognostic or predictive biomarker for VEGF antagonist therapy. VEGF-A$_{121}$ on the other hand is expected to be a more accurate biomarker for VEGF antagonist therapy.

The inventors have made the surprising discovery that levels of VEGF-A$_{121}$ can be more accurately determined in a sample by removing VEGF-A$_{165}$ from the sample using a NRP1 pull-down procedure.

Thus, in one aspect, the invention provides a method for determining the level of VEGF-A$_{121}$ in a sample, by combining the sample with NRP1, which forms a complex with the VEGF-A$_{165}$; and subsequently removing the complex from the sample, leaving behind a sample depleted of VEGF-A$_{165}$ and enriched for VEGF-A$_{121}$. The VEGF-A$_{165}$-depleted sample is then subjected to a VEGF-A quantitative assay, such as ELISA using a VEGF-A antibody, which measures the level of VEGF-A$_{121}$ remaining in the sample. In one embodiment, the NRP1 is fixed to a substrate (e.g., a well or bead), and the sample is subsequently added to the substrate. After the NRP1-VEGF-A$_{165}$ complex forms, the sample is decanted and subjected to the VEGF-A quantitative assay.

In another aspect, the invention provides a method of treating a patient suffering from a VEGF-mediate disease, including cancer or ischemia. Prior to the administration of the VEGF antagonist, the levels of VEGF-A$_{121}$ in the sample are determined by employing the NRP1 pull-down assay described above. The sample may be blood, serum, plasma, or the like.

In yet another aspect, the invention provides a method of selecting patient to be treated with a VEGF antagonist (i.e., patient stratification), a subset of which is the monitoring of a patient's response to VEGF antagonist therapy and reassessing their responsiveness to the therapy. The method comprises the step of determining the level of VEGF-A$_{121}$ in a patient, and then placing the patient either in a category of a patient who is likely to respond to VEGF antagonist treatment (category A), or in a category of a patient who is not likely to respond to VEGF antagonist treatment (category B). When the level of VEGF-A$_{121}$ is at or above a certain threshold for a particular patient, then that patient is in category A. When the level of VEGF-A$_{121}$ is below a certain threshold for a particular patient, then that patient is in category B. In some embodiments, the threshold level of VEGF-A$_{121}$ is about 15 to 20, 20 to 25, 25 to 30, 30 to 35, 35 to 40, 40 to 45, 45 to 50, 50 to 55, 55 to 60, 60 to 65, 65 to 70, 70 to 75, 75 to 80, 80 to 85, or 85 to 90 pg/mL.

In another aspect, the invention provides a method of selecting a patient capable of responding to VEGF antagonist therapy comprising the steps of (a) obtaining a biological sample from a patient; (b) determining the VEGF-A$_{121}$/VEGF-A$_{165}$ ratio in the sample; and (c) selecting a patient whose sample contains VEGF-A$_{121}$/VEGF-A$_{165}$ ratio in a range of about 0.1 to 1000, wherein said patient is more likely to respond favorably to VEGF antagonist therapy than a patient having VEGF-A$_{121}$/VEGF-A$_{165}$ ratio outside of the range.

In another aspect, the invention provides a method for treating cancer in a subject, comprising: (a) determining a VEGF-A$_{121}$/VEGF-A$_{165}$ ratio in a biological sample from said subject; and (b) based on the results of (a), administering a VEGF antagonist to the subject in need of treatment. The method comprises determining the VEGF-A$_{121}$/VEGF-A$_{165}$ ratio comprising (a) contacting a sample with a neuropilin 1 ("NRP1") protein, wherein the VEGF-A$_{165}$ binds to the NRP1 protein to form a NRP1-VEGF-A$_{165}$ complex; (b) separating the VEGF-A$_{121}$ from the NRP1-VEGF-A$_{165}$ complex to produce a VEGF-A$_{165}$-depleted fraction; (d) quantifying the VEGF-A$_{121}$ in the VEGF-A$_{165}$-depleted fraction; (e) quantifying the VEGF-A$_{165}$ in the NRP1-VEGF-A165 complex; and (f) determining the VEGF-A$_{121}$/VEGF-A$_{165}$ ratio based on the quantities in (d) and (e). In some embodiments, the ratio is about 0.001 to 1000, or about 0.01 to 1000, or about 0.1 to 100, or about 0.1 to 10, or about 1 to 10.

The patient may suffer from any one or more of an angiogenesis or VEGF-dependent disease, such as metastatic breast cancer, gastric cancer, pancreatic cancer, renal cell carcinoma, non-small cell lung cancer, androgen-independent prostate cancer, ovarian cancer, adenocarcinoma, and inter alia colorectal cancer.

DETAILED DESCRIPTION

It is to be understood that this invention is not limited to particular methods, and experimental conditions described, as such methods and conditions may vary. It is also to be understood that the terminology used in this specification is for the purpose of describing particular embodiments only, and is not intended to be limiting, since the scope of the present invention is defined by the claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure.

Unless defined otherwise, all technical and scientific terms used in this application have the same meaning as commonly understood by one of ordinary skill in the art to which this invention belongs. Although any methods and materials similar or equivalent to those described in this specification can be used in the practice of the present invention, particular methods and materials are now described. All publications mentioned herein are incorporated herein by reference in their entirety.

VEGF-A121 Assay

It is generally known that VEGF-A can serve as a predictive and prognostic biomarker for VEGF antagonist therapy; and that the predominant isoforms of VEGF in the blood are VEGF-$A_{165}$ and VEGF-$A_{121}$. It is also known that VEGF-$A_{165}$ levels show significant patient-to-patient variability, which makes it less than desirable as a biomarker. The quantification of VEGF-$A_{121}$ thus serves as a better predictive or prognostic biomarker, versus VEGF-$A_{165}$ or a mixture of the 165 and 121 isoforms.

Applicants have discovered that by adding to a sample NRP1, which forms a complex with VEGF-$A_{165}$, but not VEGF-$A_{121}$, and pulling down the resultant NRP1-VEGF-$A_{165}$ complex, the remaining supernatant was depleted of VEGF-$A_{165}$. The remaining VEGF-A in the sample was thus relatively enriched for VEGF-$A_{121}$. The total VEGF-A was then measured by a quantitative assay, such as via an anti-VEGF ELISA, and the total amount of VEGF-$A_{121}$ calculated from the total remaining VEGF-A.

Thus, in one aspect, the invention provides a method for determining the amount of VEGF-$A_{121}$ in a sample comprising the steps of (a) contacting a sample comprising VEGF-$A_{165}$ and VEGF-$A_{121}$ with a NRP1 protein, wherein the VEGF-$A_{165}$ binds to the NRP1 to form a NRP1-VEGF-$A_{165}$ complex; (b) separating the VEGF-$A_{121}$ from the NRP1-VEGF-$A_{165}$ complex to form a VEGF-$A_{165}$-depleted fraction; and (c) quantifying the VEGF-$A_{121}$ in the VEGF-$A_{165}$-depleted fraction.

The NRP1 may be fixed to a solid support. In one embodiment, the NRP1 protein is fixed to the surface of a plate or a well within a microtiter plate. In another embodiment, the NRP1 is fixed to the surface of a bead. Bead technology is well-known in the art. To affix the NRP1 protein to the bead or well or plate, the bead or well or plate is incubated with a 1 μg/mL to 10 μg/mL NRP1 protein solution. In one embodiment, the NRP1 protein solution is 10 μg/mL.

In one embodiment, NRP1 protein is covalently coupled to the surface of beads, (i.e. microspheres) such as carboxylated polystyrene microspheres by Luminex Corporation (Luminex Corporation, Austin, Tex., USA). In some embodiments, the beads are magnetic and/or emit fluorescence. Microsphere or bead kits, such as Luminex kits, are commercially available. Covalent coupling of the protein, capture, and separation of the microspheres is performed following the procedures recommended by the manufacturer. In some embodiments, an NRP1-bead pull-down method to deplete VEGF-$A_{165}$ from the sample is used in accordance with the invention described herein.

In some embodiments, the NRP1 protein is a human NRP1 protein or a fraction thereof. In some embodiments, the NRP1 protein is a fusion protein comprising of an Fc domain fused to a NRP1 domain. It is known in the art that NRP1 binds to VEGF-$A_{165}$ via its B1B2 domain, which is within the extracellular domain (ecto-domain) of NRP1 (Mamluk et al., 2002, J. Biol. Chem., 277(27):24818-24825; Nakamura et al., 1998, Neuron, 21:1083-1100). Therefore, in some embodiments, the NRP1 protein comprises the B1B2 domain. In some embodiments, the NRP1 protein comprises the ecto-domain of NRP1, which itself contains the B1B2 domain. In some embodiments, the ecto-domain or the B1B2 domain may be fused to an Fc domain, for example a mouse Fc domain or a human Fc domain (Dumont et al., 2006, Drug Development, 20(3):151-160). In one embodiment, the NRP1 protein is a NRP1-B1B2-Fc fusion protein. In another embodiment, the NRP1 protein is a NRP1-ectodomain-Fc fusion protein. NRP1 proteins are generally described in Hamerlik et al., J. Exp. Med. 2012 209(3):507-520; and Finley & Popel, AAPS J. 1 May 2012 electronic publication.

In some embodiments, prior to the pull-down step, heparin may be added to the VEGF-A-NRP1 protein admixture, which may enhance the formation of a ternary complex containing VEGF-$A_{165}$. An additional 10% or more depletion of VEGF-$A_{165}$ may be accomplished by the addition of heparin. The heparin may be at a concentration of from about 1 μg/mL to about 10 μg/mL.

The NRP1 pull-down method described herein is capable of depleting up to 75% of the VEGF-$A_{165}$. In some embodiments, at least 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74% or at least 75% of the VEGF-$A_{165}$ is depleted from the sample. After the VEGF-$A_{165}$ is depleted, the remaining VEGF-A, which is predominantly VEGF-$A_{121}$, is quantified. In some embodiments, the remaining VEGF-A is quantified via an antibody assay, such as ELISA. However, one of ordinary skill in the art in the practice of the invention may apply any method to quantify the remaining VEGF-A.

In some embodiments, the sample is a biological sample obtained from a patient. The sample may be a blood sample, or a derivative of blood, such as plasma or serum.

Methods of Treating Cancer

In one aspect, the invention provides a method of treating cancer in a patient, in which a step in the treatment regimen includes the determination of the concentration of VEGF-$A_{121}$ in the blood of the patient. The cancer may be a cancer that is likely to respond to VEGF antagonist treatment, and includes but is not limited to such cancers as metastatic breast cancer, gastric cancer, pancreatic cancer, renal cell carcinoma, non-small cell lung cancer, androgen-independent prostate cancer, metastatic androgen-independent prostate cancer, ovarian cancer, adenocarcinoma, metastatic colorectal cancer, and inter alia colorectal cancer.

In one embodiment, the method of treating cancer includes the steps of (a) obtaining a sample from a patient who suffers from cancer; (b) determining the concentration of VEGF-$A_{121}$ in the sample; and (c) administering a VEGF antagonist. The sample may be a blood sample taken from the patient, which may be subsequently separated into plasma or serum, or otherwise manipulated prior to assessing the relative levels of VEGF-$A_{121}$.

In another embodiment, the method for treating cancer in a subject, comprises: (a) determining a VEGF-$A_{121}$/VEGF-$A_{165}$ ratio in a biological sample from said subject; and (b) based on the results of (a), administering a VEGF antagonist to the subject in need of treatment.

In other embodiments, the method for treating cancer comprises determining the VEGF-$A_{121}$/VEGF-$A_{165}$ ratio comprising (a) contacting a sample with a neuropilin 1 ("NRP1") protein, wherein the VEGF-$A_{165}$ binds to the NRP1 protein to form a NRP1-VEGF-$A_{165}$ complex; (b) separating the VEGF-$A_{121}$ from the NRP1-VEGF-$A_{165}$ complex to produce a VEGF-$A_{165}$-depleted fraction; (d) quantifying the VEGF-$A_{121}$ in the VEGF-$A_{165}$-depleted fraction; (e) quantifying the VEGF-$A_{165}$ in the NRP1-VEGF-$A_{165}$ complex; and (f) determining the VEGF-$A_{121}$/VEGF-$A_{165}$ ratio based on the quantities in (d) and (e).

In some embodiments, the ratio is about 0.001 to 1000, or about 0.01 to 1000, or about 0.1 to 100, or about 0.1 to 10, or about 1 to 10. In some embodiments, the ratio is about 0.1 to about 1000. In other embodiments, the ratio is greater than about 0.1, or greater than about 10, or greater than about 100.

In still other embodiments, the biological sample is blood, plasma or serum.

In some embodiments, the VEGF-antagonist is a biotherapeutic molecule, such as a "trap", an antibody, or a fragment thereof. For example, the VEGF-antagonist may be a human or humanized monoclonal antibody that blocks VEGF activity. In some embodiments, the VEGF antagonist may be any one or more of bevacizumab, ranibizumab, aflibercept, and ramucirumab; alone or in combination with one or more other drugs. Bevacizumab is an anti-VEGF monoclonal antibody, which inhibits angiogenesis and is considered to be an anticancer drug (Los et al., 2007, The Oncologist 12(4): 443-50). Ranibizumab is a Fab fragment of the bevacizumab antibody and is used as an anti-angogenesis therapeutic (Martin et al., 2011, New England Journal of Medicine 364(20)1897-1908). Aflibercept is a "VEGF-Trap" molecule, comprising the extracelluar domains of VEGFR-1 and VEGFR-2, and the Fc region of immunoglobulin G (IgG) (Takahashi, 2011, Biol. Pharm. Bull. 34(12):1785-1788). Aflibercept is an emerging first-line treatment option for androgen-independent prostate cancer and a second-line therapy for metastatic colorectal cancer (George and Moul, 2012, Prostate 72(3):338-349). Ramucirumab is a human monoclonal antibody directed against VEGFR-2, which functions as a receptor antagonist (Hsu and Wakelee, 2009, Biodrugs 23(5): 289-304).

In some embodiments, the amount of VEGF-$A_{121}$ in the patient sample is determined by contacting the sample with a NRP1 protein, wherein any VEGF-$A_{165}$ in the sample binds to the NRP1 to form a NRP1-VEGF-$A_{165}$ complex, which is subsequently separated from the remaining VEGF-$A_{121}$, which is then quantified using a standard VEGF assay.

The NRP1 protein, various embodiments of which are as described above, may be fixed to a solid support, such as e.g., beads or the surface of a plate or well. In one embodiment, the NRP1 protein is fixed to a plate or well of a microtiter plate. To fix the NRP1 protein to the well or plate, the well or plate is incubated with 1 µg/mL to 10 µg/mL NRP1 protein. In one embodiment, the NRP1 protein is at 10 µg/mL.

In some embodiments, heparin may be added to the VEGF-A-NRP1 protein admixture, which may enhance the formation of a ternary complex containing VEGF-$A_{165}$. In some cases, the heparin enhances complex formation by at least 10%. The heparin may be at a concentration of from about 1 µg/mL to about 10 µg/mL.

The NRP1 pull-down method described herein is capable of depleting up to 75% of the VEGF-$A_{165}$ in a sample. In some embodiments, at least 35%, 36%, 37%, 38%, 39%, s40%, 41%, 42%. 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74% or at least 75% of the VEGF-$A_{165}$ is depleted from the sample. After the VEGF-$A_{165}$ is depleted, the remaining VEGF-A, which predominantly comprises VEGF-$A_{121}$, is quantified. In some embodiments, the remaining VEGF-A is quantified via an antibody assay, such as ELISA. However, one of ordinary skill in the art may apply any method to quantify the remaining VEGF-A in the practice of the invention.

Patient Stratification

In one aspect, the invention provides a method for selecting a patient capable of responding to VEGF antagonist therapy comprising the steps of obtaining a sample from a patient, determining the amount of VEGF-$A_{121}$ in the sample, and determining whether the patient is likely to respond favorably to VEGF antagonist therapy. Thus, VEGF-$A_{121}$ is used as a biomarker for the diagnosis of an VEGF-dependent cancer, for the prognosis of the development of the VEGF-dependent cancer, for monitoring patient response to VEGF antagonist therapy, or to stratify patients into at least two groups: those who are more likely to respond to VEGF antagonist therapy, and those who are not.

In another aspect, the invention provides a method of selecting a patient capable of responding to VEGF antagonist therapy comprising the steps of (a) obtaining a biological sample from a patient; (b) determining the VEGF-$A_{121}$/VEGF-$A_{165}$ ratio in the sample; and (c) selecting a patient whose sample contains VEGF-$A_{121}$/VEGF-$A_{165}$ ratio in a range of about 0.1 to 1000, wherein said patient is more likely to respond favorably to VEGF antagonist therapy than a patient having VEGF-$A_{121}$/VEGF-$A_{165}$ ratio outside of the range.

In some embodiments, the ratio is about 0.001 to 1000, or about 0.01 to 1000, or about 0.1 to 100, or about 0.1 to 10, or about 1 to 10. In other embodiments, the ratio is greater than about 0.1, or greater than about 10, or greater than about 100.

In still other embodiments, the biological sample is blood, plasma or serum

In some embodiments, the patient suffers from a cancer or other angiogenesis-related disease, such as ischemia. Those cancers to which the invention is directed for example include but are not limited to metastatic breast cancer, gastric cancer, pancreatic cancer, renal cell carcinoma, non-small cell lung cancer, androgen-independent prostate cancer, metastatic androgen-independent prostate cancer, ovarian cancer, adenocarcinoma, metastatic colorectal cancer and inter alia colorectal cancer.

In some embodiments, the VEGF antagonist therapy includes the administration of a biotherapeutic molecule alone or in combination with another cancer therapeutic (e.g., pacitaxel). Exemplary VEGF antagonist biotherapeutics include bevacizumab, ranibizumab, aflibercept, and ramucirumab, as described above.

In some embodiments, a favorable response to VEGF antagonist therapy means the slowing of the rate of growth of cancer in the patient. In some embodiments, a favorable response means the ability to enhance the effects of another chemotherapy. In some embodiments, a favorable response is the extension of life.

For patient stratification, a patient is selected as a prospective responder to VEGF antagonist therapy by determining whether the levels of VEGF-$A_{121}$ in her circulation meets or exceeds a particular threshold level. The level of the VEGF-$A_{121}$ biomarker is determined in a NRP1 pull-down assay as described above and exemplified below.

The ratio of VEGF-$A_{121}$ to VEGF-$A_{165}$ in blood, plasma, or serum may also be used for patient stratification, diagnosis and prognosis, and predicting whether a patient will respond to VEGF antagonist therapy. The expression level of the VEGF-$A_{121}$ biomarker and that of the VEGF-$A_{165}$ biomarker is determined in the NRP1 pull-down assay as described herein, and the ratio is calculated based on the molar amount of each species in the patient sample. As used hereinafter, the term "VEGF-$A_{121}$/VEGF-$A_{165}$ ratio" refers to the number of moles of VEGF-$A_{121}$ protein divided by the number of moles of VEGF-$A_{165}$ protein in the sample (plasma, serum, blood or the like). The level of VEGF-$A_{121}$ and VEGF-$A_{165}$ in a sample can be measured by any method known in the art designed to specifically measure the different VEGF-A isoforms. In certain embodiments, the levels of VEGF-$A_{121}$ and VEGF-$A_{165}$ protein in a biological sample are determined by separately measuring the levels of VEGF-$A_{121}$ and VEGF-$A_{165}$ protein using the NRP-1 pull-down assay described herein.

In one embodiment, the VEGF-$A_{121}$ is quantified in the sample following the NRP1-VEGF-$A_{165}$ pull-down procedure. In another embodiment, the VEGF-$A_{165}$ is quantified from the NRP1-VEGF-$A_{165}$ complex separated from the sample. Other methods known by one of ordinary skill in the art may be used to determine the VEGF-$A_{121}$/VEGF-$A_{165}$ ratio in a biological sample, and the NRP-1 pull-down assay is one example.

In one embodiment, the VEGF-$A_{121}$/VEGF-$A_{165}$ ratio is about 0.001 to about 1000. In some embodiments, the VEGF-$A_{121}$/VEGF-$A_{165}$ ratio is about 0.01 to about 1000. In other embodiments, the VEGF-$A_{121}$/VEGF-$A_{165}$ ratio is about 0.1 to about 100. In certain embodiments, the ratio is between the range of about 0.1 to about 10, or about 1 to about 10, or about 1 to about 100. In some embodiments, the ratio is about 1, 2, 3, 4, 5, 6, 7, 8, 9, or 10.

In some embodiments, the VEGF-$A_{121}$/VEGF-$A_{165}$ ratio is about 10 to about 100. In some embodiments, the VEGF-$A_{121}$/VEGF-$A_{165}$ ratio is about 100 to about 200. In other embodiments, the VEGF-$A_{121}$/VEGF-$A_{165}$ ratio is about 200 to about 300, or about 300 to about 400, or about 400 to about 500, or about 500 to about 600, or about 600 to about 700, or about 700 to about 800, or about 800 to about 900, or about 900 to about 1000.

In some embodiments, the VEGF-$A_{121}$/VEGF-$A_{165}$ ratio is greater than about 0.1, about 0.2, about 0.3, about 0.4, about 0.5, about 0.6, about 0.7, about 0.8, about 0.9, or greater than about 1. In some embodiments, the VEGF-$A_{121}$/VEGF-$A_{165}$ ratio is greater than about 1, about 2, about 3, about 4, about 5, about 6, about 7, about 8, about 9, or greater than about 10. In some embodiments, the VEGF-$A_{121}$/VEGF-$A_{165}$ ratio is greater than about 10, about 20, about 30, about 40, about 50, about 60, about 70, about 80, about 90, or greater than about 100.

The inventors envision that the ratio of VEGF-$A_{121}$ to VEGF-$A_{165}$ in a patient sample (blood, serum, plasma, or the like) is useful for selecting a patient who will likely benefit from or respond to VEGF antagonist therapy. The VEGF-$A_{121}$/VEGF-$A_{165}$ ratio is also envisioned to be a biomarker for the diagnosis of an VEGF-dependent cancer, for the prognosis of the development of the VEGF-dependent cancer, for the prognosis of the survival of the patient suffering from VEGF-dependent cancer, for monitoring patient response to VEGF antagonist therapy, or to stratify patients into at least two groups: those who are more likely to respond to VEGF antagonist therapy, and those who are not.

Patients with increased pretreatment circulating levels of VEGF-A were more sensitive to treatment and were shown to correlate with better prognosis of cancer survival, such as increased progression-free survival and overall survival (Miles et al, D. et al., Jul. 10, 2010, *J Clin Oncology* 28(20): 3239-3247; Van Cutsem, et al. Jun. 10, 2012, *J Clin Oncology* 30(17):2119-2127; Lambrechts et al., Mar. 20, 2013, *J Clin Oncology*, 31(9):1219-1230). Direct protein quantification methods selective for only VEGF-$A_{121}$ have not been identified. An ELISA assay, which may preferentially identify shorter VEGF forms, but also identifies longer VEGF-A isoforms, has been used as a prognostic or predictive biomarker (see International Publication Nos. WO2012010547, WO2012010548 and WO2012010550). A more selective method which identifies and quantifies both VEGF-$A_{121}$ protein and VEGF-$A_{165}$ protein in a biological sample is therefore highly desirable. Without wishing to be bound by any one theory, a ratio of the two predominant forms of circulating VEGF-A protein, i.e. VEGF-$A_{121}$ and VEGF-$A_{165}$, is envisioned to be a more accurate biomarker (as a diagnostic, prognostic, and treatment response biomarker) for patients afflicted with a VEGF-dependent cancer. The method described herein therefore provides a simple and robust assay for the measurement of such biomarkers.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Depletion Studies

VEGF-$A_{165}$ was diluted in PBS 0.5% BSA, and then transferred to an ELISA plate coated with either an NRP1-Fc fusion protein or BSA control. Some wells were coated with 1 μg/mL, and others with 10 μg/mL of a NRP1-Fc fusion protein. Two different NRP1-Fc fusion protein constructs were employed here: (1) NRP1-ecto-mFc, which comprises the ectodomain of human NRP1 (see Nakamura et al., Neuron 1998, 21:1093-1100) fused to murine Fc; and (2) NRP1-B1B2-mFc, which comprises the B1B2 domains of human NRP1 (see Mamluk et al., J. Biol. Chem. 2002, 27(5):24818-24825) fused to murine Fc. 100, 200, or 400 ρg/mL of the VEGF-$A_{165}$ was applied to the coated wells and incubated for four hours or overnight to allow for binding between VEGF- $A_{165}$ and NRP1 to occur. The well supernatants were removed and the levels of VEGF-$A_{165}$ remaining in those supernatants were determined by ELISA.

The results are presented in Table 1. To summarize, as much as 67% and 57% of the VEGF-$A_{165}$ was depleted in the wells coated in 10 μg/mL and 1 μg/mL NRP1-ecto-mFc, respectively. In addition, 10 μg/mL NRP1-B1B2-mFc depleted as much as 59% of the VEGF-$A_{165}$.

TABLE 1

| Coating | Starting Concentration of VEGF$_{165}$ (pg/mL) | Well | Remaining Concentration (pg/mL) | Average Remaining Concentration ± SD | Depletion of VEGF$_{165}$ |
| --- | --- | --- | --- | --- | --- |
| NRP1-ecto-mFc (1 μg/mL) | 400 | A1 | 220 | 190 ± 42 | 53% |
|  |  | A2 | 160 |  |  |
|  | 200 | B1 | 90 | 90 ± 0.6 | 55% |
|  |  | B2 | 89 |  |  |
|  | 100 | C1 | 47 | 43 ± 6 | 57% |
|  |  | C2 | 39 |  |  |
| NRP1-ecto-mFc (10 μg/mL) | 400 | A3 | 170 | 159 ± 15 | 60% |
|  |  | A4 | 148 |  |  |
|  | 200 | B3 | 75 | 72 ± 4 | 64% |
|  |  | B4 | 69 |  |  |
|  | 100 | C3 | 35 | 34 ± 2 | 67% |
|  |  | C4 | 32 |  |  |
| NRP1-B1B2-mFc (1 μg/mL) | 400 | D1 | 253 | 238 ± 22 | 40% |
|  |  | D2 | 222 |  |  |
|  | 200 | E1 | 121 | 122 ± 1.5 | 39% |
|  |  | E2 | 123 |  |  |
|  | 100 | F1 | 70 | 65 ± 7 | 36% |
|  |  | F2 | 60 |  |  |
| NRP1-B1B2-mFc (10 μg/mL) | 400 | D3 | 230 | 214 ± 23 | 46% |
|  |  | D4 | 197 |  |  |
|  | 200 | E3 | 112 | 107 ± 7.2 | 47% |
|  |  | E4 | 102 |  |  |
|  | 100 | F3 | 41 | 41 ± 1 | 59% |
|  |  | F4 | 42 |  |  |
| 0.5% BSA | 400 | A5 | 318 | 323 ± 7.4 | 20% |
|  |  | A6 | 328 |  |  |
|  | 200 | B5 | 167 | 166 ± 1.2 | 17% |
|  |  | B6 | 165 |  |  |
|  | 100 | C5 | 77 | 73 ± 5 | 27% |
|  |  | C6 | 70 |  |  |

Example 2

Selective Depletion Analysis

The differential effect of NRP1 binding on VEGF-$A_{165}$ versus VEGF-$A_{121}$ was determined in a plate pull-down assay. Plates were coated with 10 μg/mL human NRP-1 in phosphate buffered saline and 0.5% bovine serum albumin (BSA). Various concentrations of VEGF-$A_{165}$ or VEGF-$A_{121}$ were incubated in the coated plates for four hours to overnight. The results are presented in Table 2. In summary, from about 38% to about 65% of the VEGF-$A_{165}$ was depleted by the hNRP-1; whereas, no more than about 21% of the VEGF-$A_{121}$ was depleted. The amount of VEGF-A remaining in the supernatants post-hNRP1 pull-down was determined via ELISA.

TABLE 2

| Starting concentration of VEGF isoform (pg/mL) | Post-hNRP-1 pull-down concentration (pg/mL) | Percent change |
| --- | --- | --- |
| VEGF-$A_{165}$ | | |
| 250 | 90.1 | −65% |
| 125 | 49.8 | −58% |
| 62.5 | 25.3 | −54% |
| 31.3 | 14.3 | −52% |
| 15.6 | 8.1 | −57% |
| 7.8 | 6.2 | −38% |
| 3.9 | 3.4 | −60% |
| VEGF-$A_{121}$ | | |
| 250 | 196.39 | −21% |
| 125 | 107.17 | −15% |
| 62.5 | 56.39 | −10% |
| 31.3 | 30.70 | −5% |
| 15.6 | 16.39 | 4% |
| 7.8 | 10.18 | 31% |
| 3.9 | 6.30 | 62% |

Example 3

VEGF-$A_{165}$ Depletion in Plasma or Serum

The differential effect of NRP1 binding on VEGF-$A_{165}$ and VEGF-$A_{121}$ in a plate pull-down assay was determined. Plates were coated with 10 μg/mL human NRP-1 in phosphate buffered saline and 0.5% bovine serum albumin (BSA). Various concentrations of VEGF-$A_{165}$ or VEGF-$A_{121}$ (250, 125, 62.5, 31.3, 15.6, 7.8, and 3.9 pg/mL) were prepared in (a) assay diluent, (b) assay diluent +50% v/v pooled human plasma, (c) assay diluent +10% v/v pooled human plasma, (d) assay diluent +50% v/v pooled human sera, and (e) assay diluent +10% v/v pooled human sera. These VEGF-A solutions were incubated in the coated plates for four hours to overnight. The average percent depletion from all concentrations of VEGF-A isoforms are presented in Table 3. The amount of VEGF-A remaining in the supernatants post-hNRP1 was determined via ELISA.

Example 4

Depletion Ratios

Various ratios of VEGF-$A_{165}$ to VEGF-$A_{121}$ were made in assay diluent and subjected to hNRP1 pull-down, as described in Examples 2 and 3. The results are presented in Table 4, which demonstrates the selective pull-down of the 165 isoform over the 121 isoform of VEGF-A.

TABLE 3

| Protocol | Average percent depletion VEGF-$A_{165}$ | Average percent depletion VEGF-$A_{121}$ |
| --- | --- | --- |
| Diluent | 67-70% | 11-12% |
| 50% plasma | 67-70% | NA |
| 10% plasma | 70-75% | 12-13% |
| Diluent | 65-70% | NA |
| 50% sera | 60-65% | NA |
| 10% sera | 70-72% | NA |

TABLE 4

| Ratio | Percent loss of VEGF-$A_{total}$ |
| --- | --- |
| VEGF-$A_{165}$ (225 pg/mL):VEGF-$A_{121}$ (25 pg/mL) | 70% |
| VEGF-$A_{165}$ (125 pg/mL):VEGF-$A_{121}$ (125 pg/mL) | 40% |
| VEGF-$A_{165}$ (25 pg/mL):VEGF-$A_{121}$ (225 pg/mL) | 12% |

What is claimed is:

1. A method for enriching the amount of VEGF-$A_{121}$ in a blood sample comprising (a) contacting the sample comprising VEGF-$A_{165}$ and VEGF-$A_{121}$ with (i) a neuropilin 1 ("NRP1") protein, or (ii) a fraction of the NRP1 protein comprising the B1B2 domain, wherein the VEGF-$A_{165}$ binds to the NRP1 protein or fraction thereof to form a NRP1-VEGF-$A_{165}$ complex; (b) separating the sample from the NRP1-VEGF-$A_{165}$ complex to form a VEGF-$A_{165}$-depleted sample; and (c) quantifying the total remaining VEGF-A in the VEGF-$A_{165}$-depleted sample; wherein the total remaining VEGF-A is enriched for VEGF-$A_{121}$.

2. The method of claim 1, wherein the NRP1 protein or fraction thereof is fixed to a substrate prior to step (a).

3. The method of claim 2, wherein the substrate is a bead, a plate or a well of a microtiter plate.

4. The method of claim 3, wherein the bead, plate or well is coated with a solution of NRP1 protein.

5. The method of claim 4, wherein the bead, plate or well is coated with NRP1 protein by applying a 1 μg/mL-10 μg/mL solution of NRP1 protein to the bead, plate or well.

6. The method of claim 1, wherein the NRP1 protein is human NRP1.

7. The method of claim 1, wherein the NRP1 protein is a fusion protein comprising a NRP1 protein domain comprising a B1B2 domain and an Fc domain.

8. The method of claim 7, wherein the NRP1-fusion protein consists essentially of NRP1 domains B1 and B2 fused to an Fc domain.

9. The method of claim 7, wherein the NRP1-fusion protein consists essentially of the extracellular domain of NRP1 fused to an Fc domain.

10. The method of claim 1, wherein the sample is additionally contacted with heparin at step (a).

11. The method of claim 10, wherein the heparin is at a concentration of about 1-10 μg/mL.

12. The method of claim 1, wherein the VEGF-$A_{165}$-depleted sample contains less than 65% of the VEGF-$A_{165}$ of the non-depleted sample.

13. The method of claim 1, wherein the VEGF-A165-depleted sample contains less than 34% of the VEGF-$A_{165}$ of the non-depleted sample.

14. The method of claim 1, wherein the blood sample is a derivative of blood.

15. The method of claim 1, wherein the total remaining VEGF-A is quantified via ELISA using an anti-VEGF antibody.

* * * * *